United States Patent [19]

Torisu et al.

[11] 4,395,319

[45] Jul. 26, 1983

[54] LEAN SENSOR

[75] Inventors: Yoshio Torisu; Shigenori Sakurai; Takashi Kamo; Toshinobu Furutani, all of Toyota, Japan

[73] Assignee: Toyota Jidosha Kogyo Kabushiki Kaisha, Aichi, Japan

[21] Appl. No.: 377,017

[22] Filed: May 11, 1982

[30] Foreign Application Priority Data

May 11, 1981 [JP] Japan ................................. 56-70440

[51] Int. Cl.$^3$ ........................................... G01N 27/58
[52] U.S. Cl. ..................................... 204/426; 204/1.5; 204/429
[58] Field of Search ............................. 204/195 S, 1 S

[56] References Cited

U.S. PATENT DOCUMENTS

| 4,277,323 | 7/1981 | Muller et al. | 204/195 S |
| 4,282,080 | 8/1981 | Muller et al. | 204/195 S |
| 4,294,679 | 10/1981 | Maurer et al. | 204/195 S |
| 4,334,974 | 6/1982 | Muller et al. | 204/195 S |

FOREIGN PATENT DOCUMENTS 2075690 11/1981 United Kingdom .

Primary Examiner—Thomas A. Waltz
Assistant Examiner—B. J. Boggs, Jr.
Attorney, Agent, or Firm—Oblon, Fisher, Spivak, McClelland & Maier

[57] ABSTRACT

A lean sensor for sensing oxygen concentration in exhaust emissions, including a sensor element consisting of a tabular solid electrolyte having opposed sides provided with electrodes with at least one surface thereof coated with a porous coating layer, an element fixing plate having an element fitting hole to which the element is fitted, and a pair of heat-resistant insulating support plates having opposing windows and clamping therebetween the element fixing plate together with the sensor element disposed in the windows. In this way, it is possible precisely to locate the element in relation to the plate and to improve the bonding strength and reliability while reducing the size of the sensor as a whole.

11 Claims, 6 Drawing Figures

LEAN SENSOR

BACKGROUND OF THE INVENTION

1. Field of the Invention

This invention relates to an oxygen sensor for cleaning exhaust emissions from internal combustion engines, and more particularly to a lean sensor capable of sensing low concentrations of oxygen.

2. Description of the Prior Art

It is well known to use an oxygen sensor for cleaning exhaust emissions from internal combustion engines, particularly automobile engines.

One known oxygen sensor makes an efficient use of a phenonmenon wherein a solid electrolyte permits oxygen ion to permeate therethrough when a voltage is applied across the solid electrolyte. Namely, the oxygen concentration in the exhaust gas is detected from a threshold electric current by limiting the rate of flow of oxygen gas into the solid electrolyte. This type of oxygen sensor can easily be produced by forming electrode layers on both sides of a tabular solid electrolyte for applying a voltage across the latter, and providing a heat-resistant inorganic coating layer on at least one of the electrode layers. In addition, it is not necessary to use any reference gas as has been necessary in the conventional oxygen sensors. For these reasons, the oxygen sensing element of this type can be made extremely small in size. Furthermore, this type of oxygen sensor can be used as a lean sensor capable of sensing an extremely low concentration of oxygen.

In the production of the oxygen sensor of the type described above, however, special provisions must be made for attaching of the lead wires, supporting of the sensor element by a support and for preventing short-circuiting by carbon, because the sensor element has an extremely small diameter of 3 to 20 mm and a small thickness of 0.3 to 2 mm. In the conventional oxygen sensor of this kind, the output lead line is directly connected to the surface electrode on the element, so that the mechanical strength of this connection is extremely low, resulting in decreased reliability of operation against vibration and impact. In addition, the known oxygen sensor of this kind has suffered a problem of lack of stability of the support of the element and short-circuiting due to carbon.

A lean sensor as shown in FIGS. 5 and 6 has been proposed to obviate the above-described problems of the prior art. This lean sensor has a solid electrolyte element 1 made of zirconia stabilized by yttrium oxide or the like. The element 1 has a tubular form and a thickness ranging between 0.3 and 2 mm, and is provided at both its sides with electrodes 2 and 3 made of, for example, platinum. The element 1 is disposed between support plates 4 and 5 which are made of an insulating material having a high mechanical strength and high resistance to heat, e.g. alumina. The plate 4 and the plate 5 are bonded to each other by a heat-resistant bond 14 such as an inorganic bond. The plates 4 and 5 are provided with windows 4' and 5' of an area slightly smaller than the area of the element 1. After the element 1 is clamped between the plates 4 and 5, the windows and the portions of the plates 4, 5 around the windows are coated by coating layers 15 such as of alumina spinel which covers the element 1. Thin metallic films 8 and 9 such as of platinum are formed on the surfaces of the plates 4 and 5 adjacent to the element. The thin metallic film 8 is connected to the element electrode 2 while the thin metallic film 9 is connected to the element electrode 3 thereby to serve as lead wires. Thin metallic films 10 and 11 are formed on either one or both of the plates 4 and 5, and are coated by protective layers 12 and 13 formed thereon. Thin metallic films 10 and 11, made of platinum or the like, serve as heaters for heating the element when supplied with electric power or voltage.

In this lean sensor, however, the element cannot be located in a stable manner because the gap between the plates 4 and 5 is filled with a bond 14 by which the element 1 is fixed. In addition, since the space between two support plates is filled solely with the bond, the bonding strength between two support plates is so small that the mechanical strength of the sensor cannot be improved sufficiently. For incorporating the heaters 10 and 11 in the sensor, it is necessary to form protecting layers 12 and 13 on these heaters 10 and 11. This inconveniently makes it difficult to reduce the size of the sensor.

SUMMARY OF THE INVENTION

Accordingly, one object of this invention is to provide a new and improved lean sensor which permits precise positioning of an electrolyte element at a designated position on electrode plates.

Another object of the invention is to provide a lean sensor having an improved bonding strength and improved reliability.

Still another object of the invention is to provide a small-sized lean sensor having improved strength and reliability, suitable for use as an oxygen sensor of an exhaust gas cleaning system for cleaning exhaust gases emitted from internal combustion engines.

These and other objects are achieved according to the invention by providing a new and improved lean sensor for sensing oxygen concentration including a sensor element consisting of a tabular solid electrolyte provided on both surfaces thereof with electrodes, at least one of the electrodes having a porous coating layer provided thereon, an element-fixing plate having an element-receiving hole in which the sensor element is fitted and fixed, and a pair of heat-resistant insulating support plates having opposing windows, the element fixing plate being clamped between the support plates with the sensor element disposed in the windows.

Usable as the solid electrolyte constituting the sensor element of the lean sensor according to the invention are fine sintered bodies prepared by solidifying oxides such as $ZrO_2$, $CeO_2$, $HfO_2$, $ThO_2$, $Bi_2O_3$ or the like which are permeable to oxygen to CaO, MgO, $Y_2O_3$, $Yb_2O_3$, $Gd_2O_3$ and so on as a solid solution.

For forming the electrodes on the surfaces of the sensor element, Pt, Rn, Pd, Au, Ag and so forth are deposited to these surfaces by ion plating, chemical plating, electroplating, combination of chemical plating and electroplating, baking of metal paste, thermal decomposition of metal salt, high-frequency spattering and so forth.

The porous coating layer for limiting the amount of $O_2$ coming from the electrode into the sensor element is formed by melting and spraying a heat-resistant inorganic material such as $ZrCaO_3$, $MgAl_2O_4$ and $\alpha\text{-}Al_2O_3$ on the surface of the element. The coating layer can be formed on one or both of the electrode surfaces. Preferably, however, the coating layer is formed by melting and spraying around the windows and the peripheries of the windows so as to cover the surfaces of the elements after fixing the sensor elements to the designated position on the plates.

Heat-resistant and insulating materials such as ceramics, e.g. alumina glass, glasses, heat-resistant plastics are usable as the materials of the support plate and fixing plate. The support plates, fixing plate and the element are bonded to each other after they are put into predetermined positional relationship.

In the case where the plate is made of alumina, an inorganic bond formed from water glass with suitable aggregate is used as the bonding agent.

According to the invention, the sensor element is clamped by the support plates through the medium of the fixing plate, so that the element can be precisely located in relation to the plates and fixed easily, thereby to improve the bonding strength and the reliability of operation of the sensor.

The lead wires can be brought out from the electrodes by a suitable method. For instance, a lead wire easy to provide and having a high mechanical strength can be made by forming a thin metal film on the inner surface of the plate and connecting the end of the thin film to the electrode on the element surface. The thin metallic film can conveniently be formed by baking of metal paste. In order to prevent corrosion of the lead wires by the hot exhaust gas, the thin metal film is formed of Pt or Pt/Rh alloy containing 3 to 30 wt% of Rh.

In order to assure a sufficiently high sensitivity, it is necessary that the sensor element is heated during use up to a temperature of for example, 700° to 900° C. To this end, a thin film of Pt, W or the like material is formed as a heater on the surface of the fixing plate by printing or by baking simultaneously with the forming of the fixing plate. Thus, in the lean sensor of the invention, the heater can be formed integrally with the fixing plate, so that the size of the sensor can be reduced remarkably. By forming the heater between a plurality of fixing plates as in the case of a second embodiment which will be described hereinafter, it is possible to completely eliminate shortcircuiting between the lead wire and the heater.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
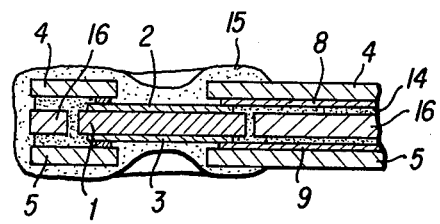
FIG. 1 is a cross-sectional view of a lean sensor constructed in accordance with one embodiment of the invention.
Figure 2:
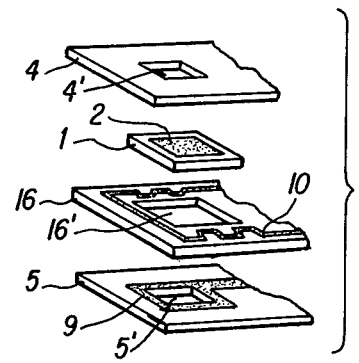
FIG. 2 is an exploded perspective view of the lean sensor as shown in FIG. 1.

Referring now to the drawings, wherein like reference numerals designate identical or corresponding parts throughout the several views, and more particularly to FIG. 1 thereof, the lean sensor of the first embodiment of the invention has a sensor element 1 consisting of a solid electrolyte such as zirconia stabilized by yttrium oxide or the like. The sensor element 1 has a generally tabular form and is provided on both surfaces thereof with electrodes 2 and 3 made of, for example, platinum.

The element 1 is fitted to an element fixing plate 16 made of an alumina insulating material having high mechanical strength and resistance to heat. The element fixing plate 16 is provided with an element receiving hole 16′ sized to receive the element 1. The element-fixing plate 16 has a thickness equal to or somewhat smaller than the thickness of the element 1. In the described embodiment, the thickness of the element 1 and the fixing plate 16 are selected to be 1 mm and 0.8 mm, respectively. The element fixing plate 16 to which the element 1 is fitted is disposed between support plates 4 and 5 made of a heat-resistant material and is bonded to these support plates 4 and 5 by means of a heat-resistant bonding agent 14 such as an inorganic bond. The plates 4 and 5 are provided with windows 4′ and 5′, respectively. After clamping the element fixing plate 16 between the support plates 4 and 5 together with the sensor element 1, the windows and the periphery of these windows are coated with coating layers 15 of alumina spinel or the like in such a manner that both surfaces of the sensor element are covered by the coating layers 15.

The surfaces of the plates 4 and 5 adjacent to the element 1 are beforehand coated with thin metal films 8 and 9 of, for example, platinum. These thin metal films 8 and 9 are connected to the element electrodes 2 and 3, respectively. The element fixing plate 16 is coated at one or both sides thereof with thin metal films 10 and 11 which serve as heaters for heating the element when supplied with a voltage.

The lean sensor of the first embodiment thus formed well satisfies the objects of the invention stated before.

Figure 3:
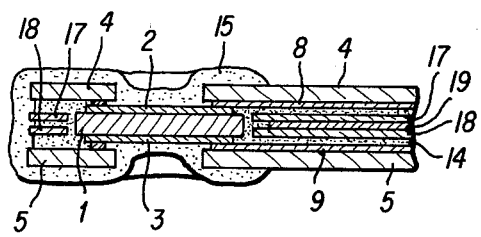
FIG. 3 is a cross-sectional view of a lean sensor constructed in accordance with another embodiment of the invention.
Figure 4:
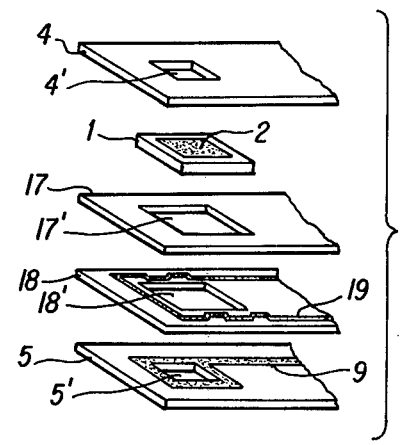
FIG. 4 is an exploded perspective view of the lean sensor as shown in FIG. 3.
Figure 5:
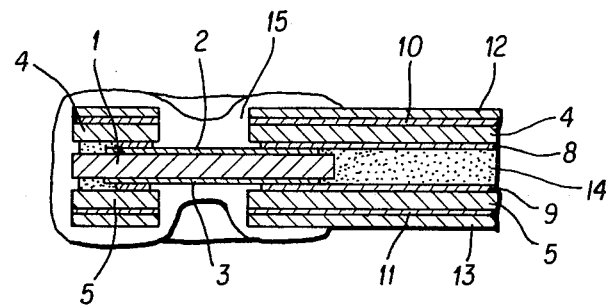
FIG. 5 is a cross-sectional view of a conventional lean sensor.
Figure 6:
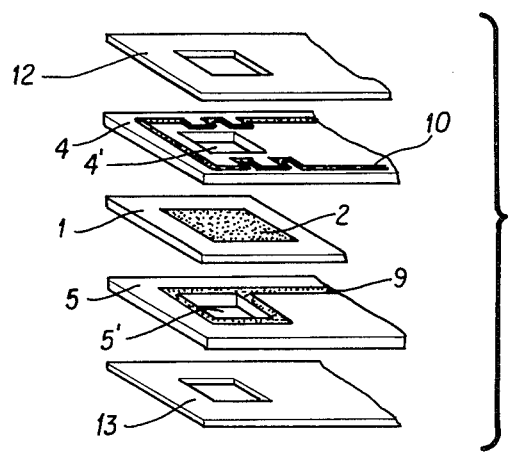
FIG. 6 is an exploded perspective view of the lean sensor as shown in FIG. 5.

As shown in FIGS. 3 and 4, a second embodiment of the invention includes an element 1 fitted to element-fixing plates 17 and 18 which are made of an insulating material having a high mechanical strength and resistance to heat. In this second embodiment, two element-fixing plates each having a thickness smaller than half of that of the element 1 are used. The fixing plates 17 and 18 are provided with receiving holes 17′ and 18′ which are sized to receive the element 1. Thus, the element 1 is fitted in the receiving holes 17′ and 18′ in the state where the fixing plates 17 and 18 are superposed to each other. The element 1 has a thickness of 1 mm, while each of the fixing plates 17 and 18 has a thickness of 0.4 mm. The element fixing plates 17 and 18 to which element 1 have been fitted are placed between support plates 4 and 5 which are made of a heat-resistant insulating material and are bonded to the support plates 4 and 5 by means of a heat-resistant inorganic bond 14 having a commercial name of Aron ceramic D. A thin metallic film 19 such as of platinum is beforehand formed on either one or both of the element-fixing plates 17 and 18, so as to serve as a heater for heating the element when supplied with electric current.

The lean sensor of the second embodiment is constructed in a manner as explained above.

As has been described, according to the invention, it is possible to locate the sensor element easily and precisely at the designated position, thanks to the use of the element-fixing plate. In addition, the use of the sensor fixing plate assures a higher mechanical strength and reliability of the sensor, while permitting a reduction of size of the sensor as a whole. The lean sensor of the invention having these advantages can be produced more easily than the conventional sensors. Thus, the present invention provides a lean sensor suitable for use in the measurement of oxygen concentration in the exhaust emissions from internal combustion engines, particularly automobile engines in which the sensor has to withstand heavy thermal load and vibratory load.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A lean sensor comprising:
    a sensor element consisting of a tubular solid electrolyte having opposed sides provided with respective electrodes and at least one electrode thereof coated with a porous coating layer;
    an element-fixing plate having a receiving hole to which said sensor element is fitted; and
    a pair of heat-resistant and insulating support plates having opposing windows, said element-fixing plate to which said element is fixed being clamped between said support plates such that said sensor element is disposed in said windows.

2. A lean sensor as claimed in claim 1, wherein said support plates, fixing plate and said element are integrated by a bond after they are arranged in a predetermined positional relationship.

3. A lean sensor as claimed in claim 2, further comprising:
    lead wires formed integrally with the inner surfaces of said support plates; and
    a heater formed on at least one surface of said element-fixing plate integrally therewith.

4. A lean sensor as claimed in claim 3, wherein said element-fixing plate comprises:
    two heat-resistant insulating plates each including a heater formed integrally with an inner surface thereof.

5. A lean sensor as claimed in claim 1, wherein said solid electrolyte constituting said sensor element comprises:
    a sintered body prepared by solidifying an oxide selected from the group consisting of $ZrO_2$, $CeO_2$, $HfO_2$, $ThO_2$ and $Bi_2O_3$ to a compound selected from the group consisting of CaO, MgO, $Y_2O_3$, $Yb_2O_3$ and $Gd_2O_3$.

6. A lean sensor as claimed in claim 1, wherein said electrodes formed on the surfaces of said sensor element comprise:
    a metal selected from the group consisting of Pt, Rn, Rd, Au and Ag, said metal deposited by a method selected from the group consisting of ion plating, chemical plating, combination of chemical plating and electroplating, baking of metal paste, thermal decomposition of metal salt and high-frequency spattering.

7. A lean sensor as claimed in claim 1, further comprising:
    said porous coating layer formed by melting and spraying a heat-resistant inorganic material selected from the group consisting of $ZrCaCo_3$, $MgAl_2O_4$ and $\alpha\text{-}Al_2O_3$.

8. A lean sensor as claimed in claim 7, further comprising:
    said porous coating layer formed on only a selected one of said electrode surfaces.

9. A lean sensor as claimed in claim 7, further comprising:
    said porous coating layers formed on both electrode surfaces by melting and spraying said heat-resistant inorganic material on said windows and the peripheries of said windows so as to cover the surfaces of said element, after fixing said sensor element to a predetermined position on said plate.

10. A lean sensor as claimed in claim 1, further comprising:
    said support plates and said fixing plate made from a material selected from the group consisting of ceramics, glass and heat-resistant plastics.

11. A lean sensor as claimed in claim 3, further comprising:
    said lead wires and said heater made from platinum or an alloy containing platinum.

* * * * *